(12) United States Patent
Kirchhuebel

(10) Patent No.: US 6,733,128 B2
(45) Date of Patent: May 11, 2004

(54) MICROSCOPE FOR NONCONTACT WIDE-ANGLE VIEWING

(75) Inventor: Rainer Kirchhuebel, Asslar (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 216 days.

(21) Appl. No.: 09/981,468

(22) Filed: Oct. 16, 2001

(65) Prior Publication Data

US 2002/0044256 A1 Apr. 18, 2002

(30) Foreign Application Priority Data

Oct. 18, 2000 (DE) .................................... 200 17 891 U

(51) Int. Cl.⁷ .............................. A61B 3/10; A61B 3/02
(52) U.S. Cl. ........................ 351/205; 351/233; 351/236
(58) Field of Search ................................ 351/200, 216, 351/205, 233, 236, 245; 359/368–390

(56) References Cited

U.S. PATENT DOCUMENTS 5,076,682 A * 12/1991 Pasfield ...................... 351/158
5,219,285 A * 6/1993 Meller et al. ................ 433/126
5,589,896 A * 12/1996 Mainster et al. ............ 351/219
5,793,524 A * 8/1998 Luloh .......................... 359/381
5,825,535 A * 10/1998 Biber et al. .................. 359/380
6,010,477 A * 1/2000 Bays ............................ 604/22
6,443,973 B1 * 9/2002 Whitman .................... 606/219

FOREIGN PATENT DOCUMENTS

DE          195 41 237          5/1996

* cited by examiner

Primary Examiner—Dennis W. Ruhl
Assistant Examiner—John R Sanders
(74) Attorney, Agent, or Firm—Flynn, Thiel, Boutell & Tanis, P.C.

(57) ABSTRACT

Microscopes with a noncontact wide-angle viewing scope are used during surgeries on the eye, wherein an electromotively adjustable optic is provided between the lens and the eye. In order to prevent the surgeon from interrupting the surgery in order to refocus and to allow the electromotive drive to be maintained in a sterile condition, the drive is provided above the lens and is rotatably connected to an adjusting gear for the optic by means of a flexible drive shaft which can be released from the drive.

17 Claims, 2 Drawing Sheets

MICROSCOPE FOR NONCONTACT WIDE-ANGLE VIEWING

FIELD OF THE INVENTION

The invention relates to a microscope for the noncontact wide-angle viewing of an eye with the help of an optic which is provided between the lens of the microscope and the eye and which lies in the optic axis of the lens, and can be moved in the direction of the optic axis, during surgery on the eye, in particular, the microscope can be moved by means of a linear gear that is arranged in a device which consists of a mounting mountable on the microscope and a holding arm for the optic that can be moved on the mounting, wherein the linear gear is arranged between the mounting and the holding arm.

BACKGROUND OF THE INVENTION

A wide-angle viewing of the eye can be done in a simple manner by a contact lens that is directly placed on the eye.

An additional optic between the eye and the lens, which optic cannot be moved with reference to the lens, can only be used in a limited manner because the surgeon must often change the image plane during surgery. It is therefore important that the optic additionally mounted on the microscope can be refocused.

A microscope of this type is already known, for example, from the U.S. Pat. No. 5 793 524. A linear gear is thereby provided to help move an optic, which is provided on the holding arm, in the direction of an optic axis of the microscope relative to its lens. The holding arm includes a first rotatable gear element thereon which couples to a second linear gear element that is provided in a mounting connected to the microscope and is nonrotatable on the mounting. The linear gear can thereby consist, for example, of a threaded spindle and a spindle nut that is longitudinally movable through rotation on the threaded spindle, or of a rack and a pinion movable along the rack through rotation. Accordingly, the spindle nut or the rack each form the first gear element provided on the holding arm and the threaded spindle or the rack each form the second gear element provided on the mounting. A handle is connected to the first gear element to help rotate the first gear element so that it is indeed possible for the surgeon to also adjust the focal distance of the microscope during surgery.

Of course it is not advantageous when the surgeon, who must in most instances guide the surgical instruments with both hands during surgery on the eye and must also operate the handle to refocus. Thus, the surgeon must either interrupt the surgery to refocus or must have the refocusing done with the help of an assistant who can carry out this task only via instructions from the surgeon who is looking through the microscope. Both of these options are complicated and time-consuming.

SUMMARY OF THE INVENTION

A microscope according to the present invention does not need any auxiliary means directly provided on the eye and yet realizes a focal distance which guarantees a sufficient image field during the surgery. The surgeon has thereby available the area between the optic and the eye in order to be able to guide the surgical instruments unhindered.

One goal of the present invention is to replace the handle with an electromotive drive, the switching device of which can also be operated by the surgeon during surgery without the need to put down the surgical instruments and thus without the need to interrupt the surgery.

The basic purpose of the instant invention is to provide a microscope of the type identified in detail above in such a manner that the optic for wide-angle viewing can be refocused by the surgeon during surgery on the eye without having to interrupt the surgery, wherein the arrangement is yet such that damages through autoclaving during the necessary sterilization of the device can be avoided.

The purpose is attained according to the invention by the linear gear being operable by an electromotive drive, the output of which is connected to the linear gear through a flexible drive shaft. In this manner, it is possible to remove the electromotive drive from the area in which all other parts must be sterilized prior to each surgery. The drive shaft, unlike the electromotive drive, can be sterilized without being damaged so that the microscope according to the invention can indeed be easily switched by the surgeon during surgery without the need to interrupt such surgery, and without influencing the life span of the microscope through repeated sterilization of its parts which are exposed to the surgical area.

It is particularly advantageous, for example, when the electromotive drive is provided on the microscope in the area of the eyepiece housing. The drive can be relatively small because the drive power needed for the linear gear is very low. As a result of its correspondingly small volume, its arrangement directly on the microscope hardly interferes with its compact design and, on the other hand, it is assured that the needed flexible drive shaft can be relatively short and can be arranged so that it does not interfere during use.

When the mounting is fastened on the lens housing of the microscope, it is thereby advantageous, so that again a flexible drive shaft that is as short as possible can be realized.

In a preferred embodiment of the microscope according to the invention, the linear gear is designed as a spindle drive with a threaded spindle which is supported parallel to the optic axis and is spaced from same. The linear gear is rotatably supported on the mounting, whereby an adjusting wheel connected to the holding arm is guided longitudinally movably on the threaded spindle, and the threaded spindle can be driven by the drive shaft. The spindle nut is hereby, as a rule, fixed against rotation and is locked accordingly. The arrangement, however, can also be such that the rotary locking of the spindle nut can be disengaged so that the spindle nut can in turn be used for the manual drive of the linear gear; the flexible drive shaft must thereby not necessarily be locked fixed against rotation because it can have a sufficient automatic locking.

The entire device, which is needed on the microscope for the additional optic, the so-called BIOM-System, and which is to be newly sterilized prior to each surgery, can without any difficulties be completely separated from the microscope when the drive shaft, in particular in the area in which the electromotive drive remains on the microscope, is easily releasable.

It is particularly advantageous when the drive shaft is divided into two parts, whereby a first shaft piece is fastened to the output of the electromotive drive so that it cannot easily be removed and a second shaft piece is drivingly connected to the threaded spindle that can be easily uncoupled from the first shaft piece by means of a coupling. The coupling can be designed to be easily releasable without any difficulties so that the shaft pieces can be mounted both on the electromotive drive and also on the mounting or on the threaded spindle there supported so that they cannot be easily separated and accordingly so that the relatively fixed mechanical connections can prevent operating errors. Again, considering the sterilization of the device, it is best that the coupling of the shaft pieces is such that the coupling is always above the microscope lens. The shaft piece that is connected to the mounting is completely sterilized during autoclaving so that only the part of the drive shaft that is removed far from the area between the lens and the eye remains nonsterile.

It is convenient when setting up the microscope that a switching device for the electromotive drive is arranged in such a manner that it can be switched simultaneously with the operation of other handles of the microscope.

During surgery on the eye, it is possible for the surgeon to refocus the optic by means of a foot switch that can adjust the electromotive drive. The surgeon can hereby continue surgery with both hands without having to interrupt the procedure or use an assistant. This significantly increases the safety of the surgery while the duration of the surgery is not unnecessarily extended due to needed manipulations of the microscope. As an alternative, a hand switch which is operated by an assistant is also possible.

The optic can house a reversing prism so that the field of vision of the microscope is reflected nonreversed in the eyepiece.

Although the invention significantly improves the microscope for the intended purpose without excessive expense and in an apparatus-technically simple manner so that the function of the microscope is improved and its servicing is simplified, while all necessary parts of the microscope can be continuously and regularly sterilized.

BRIEF DESCRIPTION OF THE DRAWINGS

The invention will be discussed in greater detail hereinafter for one exemplary embodiment in connection with the drawing.

DETAILED DESCRIPTION

Figure 1:
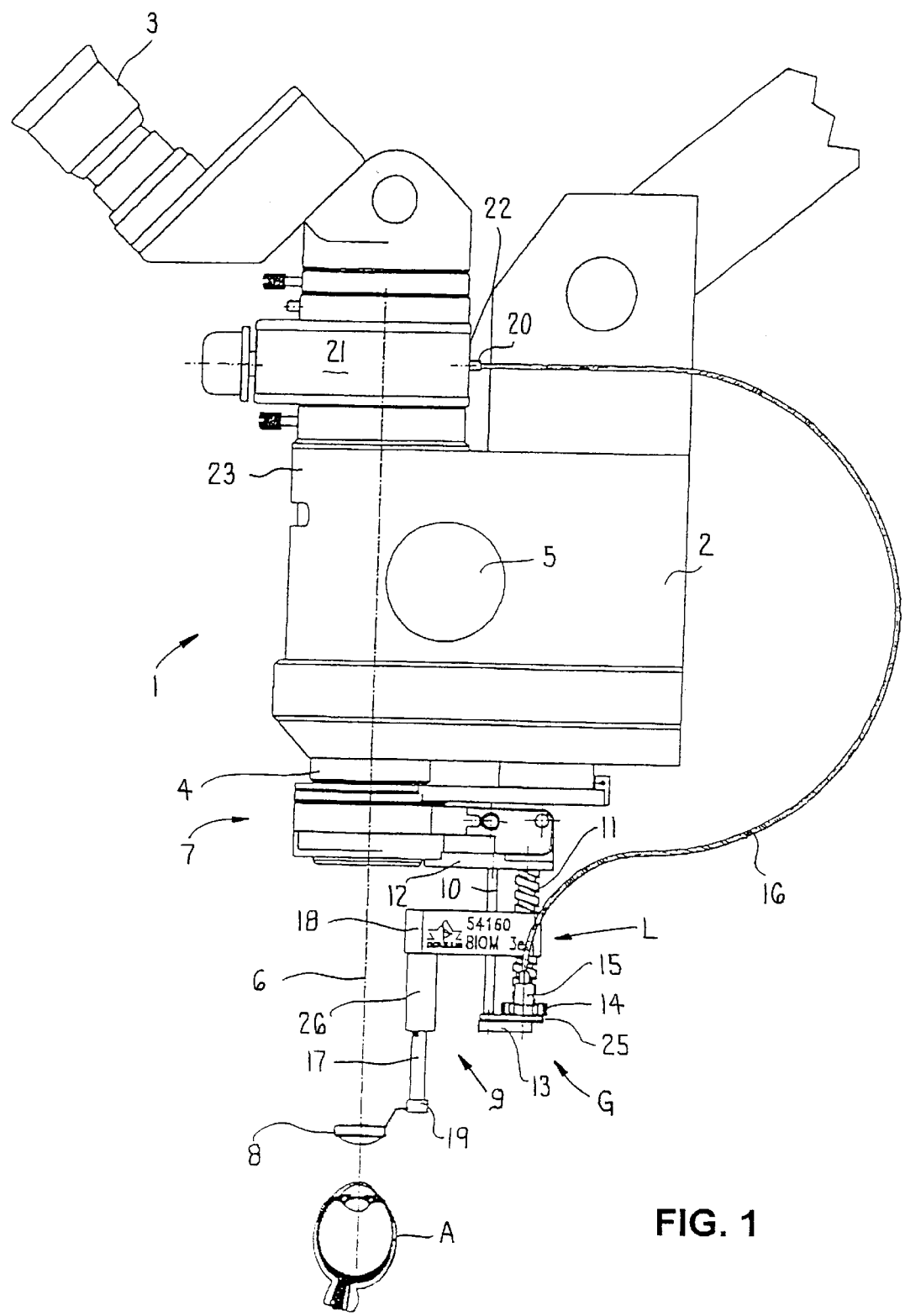
FIG. 1 is a schematic side view of a microscope according to the invention.

A microscope 1 according to the invention consists first of a housing 2 with an eyepiece 3 and a lens 4.

A mounting 7 is mounted on the lens housing, which mounting is nonmovable relative to the lens 4 in the direction of an optic axis 6 and is used to fix an optic 8 to the lens 4. The drawing illustrates the optic 8 merely as an aspherical lens, however, in addition it preferably advantageously includes a reversing prism (not shown) to facilitate nonreversed viewing. The optic 8 is provided on a holding arm 9 which is longitudinally movable on the mounting 7 in direction of the optic axis 6. A stationary rod 10 and a threaded spindle 11 are mounted on the mounting 7 for this purpose, which rod 10 and threaded spindle 11 extend parallel to the optic axis 6. The stationary rod 10 and the threaded spindle 11 are both supported at one end on a base plate 12 of the mounting 7 that is held on the lens housing 2, and the rod 10 and spindle 11 are supported at the other end on a bridge 13.

Figure 2:
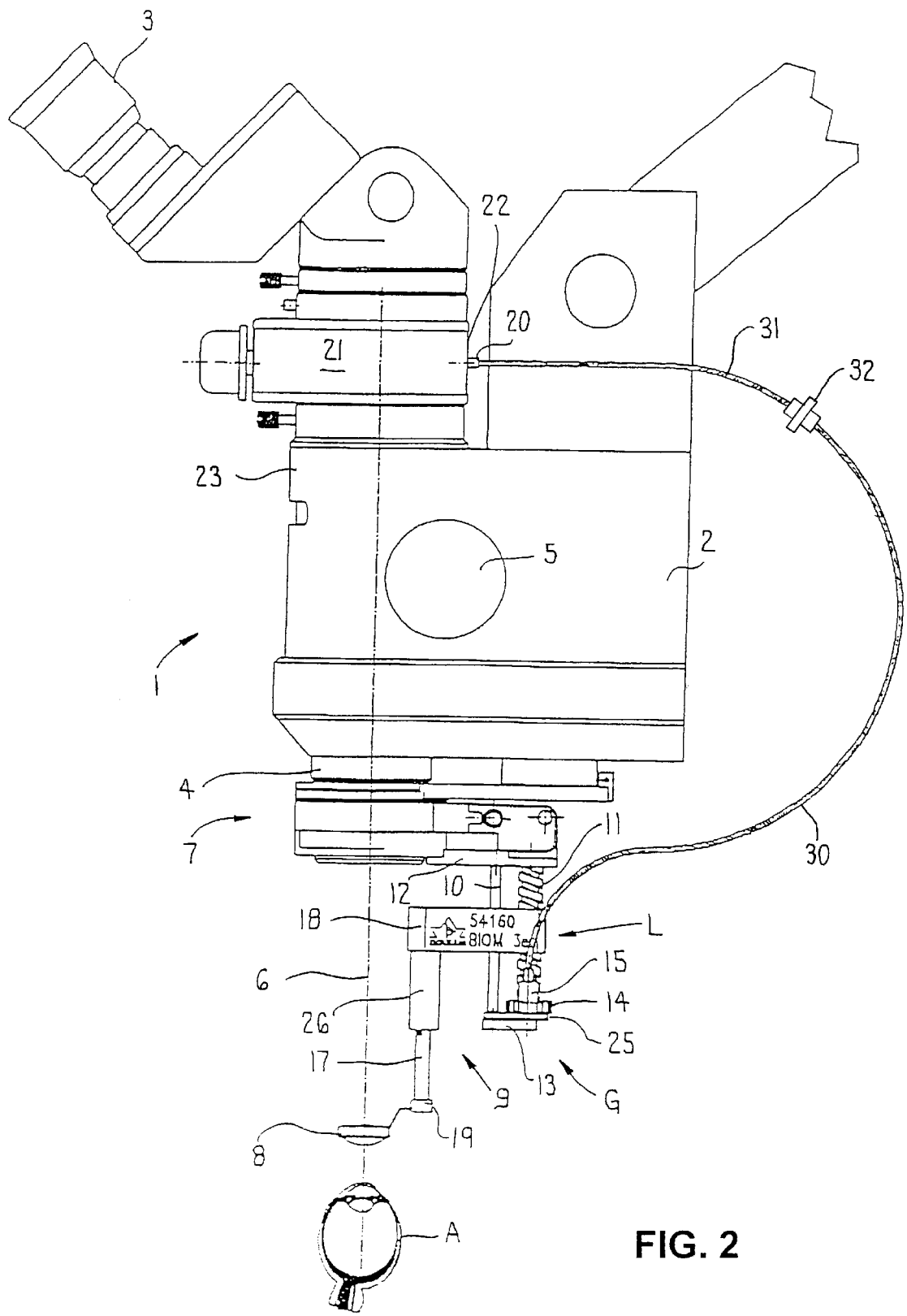
FIG. 2 is a schematic side view of a microscope according to the invention including a releasable shaft coupling.

The arrangement is mostly designed such that the optic 8 can be swung into the beam path 6 of the microscope 1 (this position is illustrated in FIGS. 1 and 2) and can again be swung out of this position; the structural details of this are known and thus are not illustrated in detail in the drawings.

The threaded spindle 11 easily rotatable, however, it is not longitudinally movable, with respect to both the base plate 12 and also the bridge 13. An adjusting wheel 14 is fixed on the threaded spindle 11. A coupling 15 for the drive shaft 16 is arranged in the bridge 13. The coupling 15, which has a disk to receive a drive belt 25, is coupled with a flexible drive shaft 16. The rotary motion of the drive shaft 16 is transmitted from the coupling 15 to the threaded spindle 11 by means of a belt drive 25.

The holding arm 9 has a traverse 18 with a guide tube 26, into which a guide rod 17 can be driven for safety reasons in case the eye to be treated is touched. A coupling with a catch 19 is provided on the guide rod 17 for exchanging various viewing lenses 8 depending on which retina or glass-member area the surgeon wants to scan.

The drive shaft 16 is coupled at its end 20 remote from the gearing G to the output 22 of an electromotive drive 21, which is fixed on the eyepiece housing 23. As an alternative, or in addition, it is possible to provide a foot switch in a conventional manner, (not shown) so that the optic 8 can be moved in the direction of the axis 6 without the need for a manual operation to take place. A hand switch for the purpose of switching over is also possible.

The arrangement is such that the drive shaft 16 can be uncoupled from the drive 21. However, as shown in FIG. 2, it is also possible to design the drive shaft 16 in two parts and to couple the thus formed two shaft pieces or elements 30, 31, which are relatively rigidly connected to the output 22 and the coupling 15, by means of a releasable shaft coupling 32 so that the shaft piece on the output 22 can remain there when the entire remaining device serving the wide-angle viewing, namely the mounting 7, holding arm 9, linear gear L, optic 8 and the remaining shaft piece of the drive shaft 16, is sterilized in an autoclave.

What is claimed is:

1. A microscope for the noncontact wide-angle viewing of an eye by an optic which is provided between a lens of the microscope and the eye and which lies in an optic axis of the lens and can be moved along the optic axis by a linear gear, said optic being arranged as part of a device, said device comprising a mounting mountable on the microscope and a holding arm for the optic, said holding arm capable of being moved on the mounting, the linear gear being arranged between the mounting and the holding arm, wherein the linear gear can be operated by an electromotive drive having an output connected to the linear gear through a flexible drive shaft, said drive shaft being divided into a first shaft piece fastened to the output of the electromotive drive so that it cannot easily be removed, and a second shaft piece drivingly connected to the linear gear and easily uncoupled from the first shaft piece by a coupling that joins the first and second shaft pieces at a location above the lens provided on the microscope.

2. The microscope according to claim 1, wherein the electromotive drive is attached to the microscope.

3. The microscope according to claim 1, wherein the electromotive drive is provided in an area of an eyepiece housing.

4. The microscope according to claim 1, wherein the mounting is fastened to a lens housing of the microscope.

5. The microscope according to claim 1, wherein the linear gear comprises a spindle drive with a threaded spindle that is supported parallel to the optic axis and spaced therefrom and is supported rotatably on the mounting, wherein an adjusting wheel connected to the holding arm is guided longitudinally movably on the threaded spindle, and the threaded spindle is driven by the drive shaft.

6. The microscope according to claim 1, wherein the electromotive drive is switched by a manual key.

7. The microscope to claim 1, wherein the electromotive drive is switched by a foot switch.

8. The microscope according to claim 1, wherein the optic includes a reversing prism.

9. A microscope and attachment for wide-angle viewing of an eye, said microscope including a microscope housing having a microscope lens with an optic axis at a lower end thereof defining a beam path and said attachment comprising:
- a mounting secured at a lower end of said microscope;
- an optic supported by a guide rod in the beam path of said microscope;
- a linear gear supported by said mounting;
- elements connecting said guide rod to said linear gear for enabling movement of said optic in opposing vertical directions;
- a motor drive having an output and located out of said microscope housing; and
- a flexible drive shaft having one end connected to the output of said motor drive and a second end connected to said linear gear for selectively moving said optic in the vertical directions.

10. The microscope and attachment according to claim 9, said flexible drive shaft comprising:
- a first shaft piece fastened to the output of said motor drive;
- a second shaft piece drivingly connected to said linear gear; and
- a drive shaft coupling that couples said first shaft piece to said second shaft piece.

11. The microscope and attachment according to claim 10, wherein said first shaft piece has a shortened length so that said first shaft piece does not extend to the microscope lens when said first shaft piece is uncoupled from said second shaft piece.

12. The microscope and attachment according to claim 11, wherein said motor drive is secured to the outside of said microscope housing.

13. The microscope and attachment according to claim 9, wherein said linear gear comprises a threaded spindle secured to a base plate of said mounting and a linear coupling for coupling said flexible drive shaft to an adjusting wheel and belt drive arrangement and a stationary rod parallel to said threaded spindle.

14. The microscope and attachment according to claim 13, said elements connecting said rod to said linear gear comprising a transverse element coacting with said threaded spindle and said stationary rod and a guide tube secured at one end to said transverse element and at an opposing end to said guide rod supporting said optic.

15. The microscope and attachment according to claim 9, wherein said motor drive is secured to the outside of said microscope housing.

16. The microscope and attachment according to claim 9, wherein said motor drive is controlled by a foot switch.

17. A microscope and attachment for wide-angle viewing of an eye, said microscope including a microscope housing having a microscope lens with an optic axis at a lower end thereof defining a beam path and said attachment comprising:
- a mounting secured at a lower end of said microscope;
- an optic element supported by a guide rod in the beam path of said microscope;
- a linear gear supported by said mounting;
- elements connecting said guide rod to said linear gear;
- a motor drive;
- a flexible drive shaft arrangement comprising:
  - a first shaft element having one end connected to an output of said motor drive;
  - a second shaft element having one end connected to said linear gear; and
  - a drive shaft coupling that couples an opposing end of said first shaft element to an opposing end of said second shaft element,
- wherein said motor drive selectively drives said flexible drive shaft arrangement to move said optic element in opposing vertical directions.

* * * * *